(12) United States Patent
Ukegawa

(10) Patent No.: US 7,972,459 B2
(45) Date of Patent: *Jul. 5, 2011

(54) METHOD FOR MAKING PULL-ON DISPOSABLE WEARING ARTICLE

(75) Inventor: Kazuo Ukegawa, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 1142 days.

This patent is subject to a terminal disclaimer.

(21) Appl. No.: 11/209,781

(22) Filed: Aug. 24, 2005

(65) Prior Publication Data

US 2006/0042746 A1    Mar. 2, 2006

(30) Foreign Application Priority Data

Aug. 31, 2004 (JP) ................................ 2004-251952
Jul. 12, 2005 (JP) ................................ 2005-202431

(51) Int. Cl.
| B29C 65/00 | (2006.01) |
| B32B 37/00 | (2006.01) |
| B32B 37/02 | (2006.01) |
| B32B 38/00 | (2006.01) |
| B32B 38/04 | (2006.01) |

(52) U.S. Cl. ......... 156/253; 156/252; 156/256; 156/227
(58) Field of Classification Search .................. 156/270, 156/204, 250, 227, 256, 163, 164, 252, 253; 428/44, 47, 48, 52
See application file for complete search history.

(56) References Cited

U.S. PATENT DOCUMENTS

| 5,766,737 | A | 6/1998 | Willey et al. |
| 6,264,643 | B1 | 7/2001 | Toyoda |
| 6,328,725 | B2 * | 12/2001 | Fernfors ..................... 604/391 |
| 6,432,248 | B1 * | 8/2002 | Popp et al. .................. 156/256 |
| 6,830,153 | B2 * | 12/2004 | French et al. ................ 206/538 |
| 7,189,301 | B2 * | 3/2007 | Otsubo et al. ............... 156/269 |
| 2001/0014798 | A1 | 8/2001 | Fernfors |

(Continued)

FOREIGN PATENT DOCUMENTS

EP    1013251 A1    6/2000

(Continued)

OTHER PUBLICATIONS

European Search Report of Application No. 05781519.3 2124 / 1792594 PCT/JP2005/015918 mailed Mar. 31, 2010.

(Continued)

*Primary Examiner* — Mark A Osele
*Assistant Examiner* — Christopher C Caillouet
(74) *Attorney, Agent, or Firm* — Lowe, Hauptman, Ham & Berner, LLP

(57) ABSTRACT

In a method for continuously making pull-on disposable wearing, a web is fed in a machine direction. The web is formed with first fastener elements on both sides of a region defining a cut line extending in a cross direction. Second fastener elements on a fastener base sheet are engaged with the respective first fastener elements, and a region between these first fastener elements is cut away from the web. Then, the web is folded in two and a side edge of the web is bonded to the fastener base sheet. Thereafter, the web is successively cut along the cut lines to separate the web into segments each of which is a pull-on wearing article having front and rear waist regions adapted to be detachably connected with each other by the first and second fastener elements.

3 Claims, 10 Drawing Sheets

U.S. PATENT DOCUMENTS

| | | | |
|---|---|---|---|
| 2002/0148557 A1* | 10/2002 | Heller et al. | 156/252 |
| 2002/0174931 A1 | 11/2002 | Couillard et al. | |
| 2003/0135184 A1 | 7/2003 | Van Gompel et al. | |
| 2004/0040642 A1 | 3/2004 | Otsubo et al. | |
| 2004/0108043 A1 | 6/2004 | Otsubo | |
| 2004/0112508 A1 | 6/2004 | Umebayashi et al. | |
| 2004/0182502 A1* | 9/2004 | Wagner et al. | 156/204 |
| 2004/0194879 A1 | 10/2004 | Ohiro et al. | |

FOREIGN PATENT DOCUMENTS

| | | |
|---|---|---|
| EP | 1813234 A1 | 8/2007 |
| GB | 2308290 A | 6/1997 |
| WO | WO 97/23180 | 7/1997 |
| WO | 0187209 A1 | 11/2001 |
| WO | WO 01/87208 | 11/2001 |
| WO | WO 01/87209 A1 | 11/2001 |
| WO | 2004016209 A1 | 2/2004 |
| WO | 2004/052258 A1 | 6/2004 |

OTHER PUBLICATIONS

European search report for EP application No. 05806959.2 mailed Jul. 6, 2009.

* cited by examiner

US 7,972,459 B2

METHOD FOR MAKING PULL-ON DISPOSABLE WEARING ARTICLE

RELATED APPLICATIONS

The present application is based on, and claims priority from, Japanese Application Number 2004-251952, filed Aug. 31, 2004 and Japanese Application Number 2005-202431, filed Jul. 12, 2005, the disclosure of which is hereby incorporated by reference herein in its entirety.

BACKGROUND OF THE INVENTION

This invention relates to a method for making pull-on disposable wearing articles provided with fastener means.

Pull-on wearing articles, including pull-on disposable diapers by way of example, have already been proposed wherein transversely opposite side edges of the front waist region are connected with those of the rear waist region by releasable and reusable fastener means. For example, WO 01/87209 A1 (REFERENCE) discloses disposable training pants 500 and a method for making the same as illustrated in FIGS. 10 and 11 accompanying the specification of this patent application. In the pants 500, each side edge of the front waist region 522 is provided on its inner surface with first fastening means 582 while each side edge of the rear waist region 524 is provided on its outer surface with second fastening means 584 adapted to cooperate with the first fastening means 582. The first fastening means 582 may comprise, for example, a hook-type fastener and the second fastening means 584 may comprise, for example, a loop-type fastener. In the process illustrated in FIG. 11, a continuous chassis web 532 contouring the pants 500 runs from the left toward the right as viewed in FIG. 11. The front waist region 522 has front waist elastic members 554 attached to its inner surface and the rear waist region 524 has rear elastic members attached to its inner surface. On both sides of a boundary line 592 extending between each pair of the adjacent pants 500, the first fastening means 582 are respectively attached and then, between these adjacent first fastening means 582, 582, the chassis web 532 is partially cut away to define a gap 579. On the inner surface of the front waist region 522, the second fastening means 584 is releasable attached to each pair of the adjacent first fastening means 582, 582 so as to extend across the gap 579. Though not illustrated, after the chassis web 532 has been folded back with the inner surface thereof inside, the inner surface of the rear waist region 524 is bonded to the second fastening means 584. Then, the chassis web 532 is cut along the boundary lines 592 to obtain individual pants 500 shown in FIG. 10.

Referring to FIG. 11, the continuous chassis web 532 runs on an endless belt from the left toward the right. While the chassis web 532 is held in close contact with the endless belt under a vacuum suction pressure, there is a possibility that the respective front waist regions 522 lined up in a machine direction successively with interposition of the gaps 579 might be affected by a tensile force serving to drive rightward. It is likely therefore that the respective front waist regions 522 might be misaligned or distorted on the endless belt. Consequentially, there is an anxiety that the front waist regions 522 of the individual pants 500 continuously output through this process might have random shapes. Compared to the case in which the chassis web 532 is still not provided with the front waist elastic members 554, the chassis web 532 having already been provided with the front waist region elastic members 554 will be more likely to suffer from this problem because of a contractile force of these elastic members 554 exerted on the chassis web 532.

SUMMARY OF THE INVENTION

In view of the problem encountered by the method for making the pull-on disposable wearing articles such as the training pants disclosed in REFERENCE wherein the transversely opposite side edges of the front waist region are connected with those of the rear waist region by the fastener means, it is an object of this invention to improve such method for making the wearing article so that the individual wearing articles continuously output may reliably have uniform shapes even if the web is partially cut away to form gaps as the continuous web is fed in one direction.

To achieve the object set forth above, the first aspect of the invention relates to a method for continuously making a plurality of pull-on disposable wearing articles comprising the steps of feeding a web defined by inner and outer surfaces and first and second side edges extending in parallel to each other in a machine direction in the machine direction, folding the web in two along a cross direction being orthogonal to the machine direction in the course of feeding the web so that the first and second side edges fall into line, then severing the web along cut lines extending in the cross direction to form segments of the web each having a given dimension in the machine direction, and releasably bonding two layers defined by each of the web segments folded in two in vicinity of transversely opposite side edges of the respective layers extending in parallel to the cut lines in the cross direction by means of fastener means to obtain a plurality of the pull-on disposable wearing articles each having a waist-hole and a pair of leg-holes so that these pull-on disposable wearing articles are successively arranged side by side in the machine direction.

The method for making such wearing articles according to the first aspect of this invention further comprises the steps as follows:

a. attaching a pair of first fastener means on an outer surface of the web adjacent to the first side edge as viewed in the cross direction and on both sides, as viewed in the machine direction, of a region in which the cut line is to be formed;

b. forming the web between the region in which the cut line is to be formed and the respective first fastener means with a pair of rectilinear slits extending in the cross direction beyond opposite ends of the first fastener means as viewed in the cross direction and opposed to each other about the region in which the cut line is to be formed;

c. attaching a fastener's base sheet piece having a pair of second fastener means extending in the machine direction across a pair of the rectilinear slits, respectively, and adapted to be releasably engaged with the first fastener means formed on the both sides of the region to the web through engagement of the respective second fastener means with respective the first fastener means;

d. forming the web in vicinity of the ends of the respective first fastener means with notches intersecting a pair of the rectilinear slits, respectively;

e. folding the web in two along the cross direction with the inner surface inside so that the first side edge and the second side edge fall into line while a region of the web surrounded at least by a pair of the rectilinear slits and the notches is cut away or retained;

f. bonding, between the region in which the cut line is to be formed and a pair of the rectilinear slits, respectively, a region of the web having been folded in two located aside toward the second side edge to the fastener's base sheet piece directly or indirectly through the intermediary of the surrounded region having been retained in the step e; and g. severing, after the step f, the web together with the fastener's base sheet pieces along the region in which the cut line is to be formed.

According to one preferred embodiment (1) of the invention based on the first aspect of the invention, the method includes a step of attaching a bodily fluid absorbent member comprising an assembly of bodily fluid absorbent materials and a liquid-pervious sheet at least partially covering a surface of the assembly to the inner surface of the web.

According to another preferred embodiment (2) of the invention based on the first aspect of the invention, prior to formation of the rectilinear-slits, elastic members extending in the machine direction are attached in stretched state to the web in vicinity of the first side edge.

To achieve the object set forth above, the second aspect of the invention relates to a method for continuously making a plurality of pull-on disposable wearing articles comprising the steps of feeding a web defined by inner and outer surfaces and first and second side edges extending in parallel to each other in a machine direction in the machine direction, folding the web in two along a cross direction being orthogonal to the machine direction in the course of feeding the web so that the first and second side edges fall into line, then severing the web along cut lines extending in the cross direction to form segments of the web each having a given dimension in the machine direction, and releasably bonding two layers defined by each of the web segments folded in two in vicinity of transversely opposite side edges of the respective layers extending in parallel to the cut lines in the cross direction by means of fastener means to obtain a plurality of the pull-on disposable wearing articles each having a waist-hole and a pair of leg-holes so that these pull-on disposable wearing articles are successively arranged side by side in the machine direction.

The method for making such wearing articles according to the second aspect of the invention further comprises the steps as follows:

a. attaching a pair of first fastener means on an outer surface of the web adjacent to the first side edge as viewed in the cross direction and on both sides, as viewed in the machine direction, of a region in which the cut line is to be formed;

b. forming the web between the region in which the cut line is to be formed and the respective first fastener means with a pair of rectilinear slits extending in the cross direction beyond opposite ends of the first fastener means as viewed in the cross direction and opposed to each other about the cut line;

c. attaching a fastener's base sheet piece having a pair of second fastener means extending in the machine direction across a pair of the rectilinear slits, respectively, and adapted to be releasably engaged with the first fastener means formed on the both sides of the region to the web through engagement of respective the second fastener means with the respective first fastener means;

d. forming the web with an annular notch bisected in the machine direction by the region in which the cut line is to be formed and intersects respective the rectilinear slits on the both sides in vicinity of the second side edge and cutting a region extending inside the annular notch away from the web;

e. forming the web with substantially arc notches on the both sides wherein each of the arc notches has its bottom intersecting the rectilinear slits at ends thereof in the vicinity of the first side edge and its tops extending to the first side edge;

f. folding the web in two along the cross direction with the inner surface inside so that the first side edge and the second side edge fall into line while a region of the web surrounded by the first side edge, a pair of the rectilinear slits formed on both sides of the region in which the cut line is to be formed, the annular notch and the arc notches intersecting the respective rectilinear slits is cut away or retained;

g. bonding, between the region in which the cut line is to be formed and a pair of the rectilinear slits, respectively, a region of the web having been folded in two located aside toward the second side edge to the fastener's base sheet piece directly or indirectly through the intermediary of the surrounded region having been retained in the step f; and h. severing, after the step f, the web together with the fastener's base sheet pieces along the region in which the cut line is to be formed.

According to one preferred embodiment (3) of the second aspect of the invention, the method includes a step of attaching a bodily fluid absorbent member comprising an assembly of bodily fluid absorbent materials and a liquid-pervious sheet at least partially covering a surface of the assembly to the inner surface of the web.

According to another preferred embodiment (4) of the second aspect of the invention, prior to formation of the rectilinear slits, elastic members extending in the machine direction are attached in stretched state to the web in vicinity of the first side edge.

According to still another preferred embodiment (5) of the second aspect of the invention, prior to formation of the annular notch, elastic members are attached in stretched state to the web along a region in which the annular notch is to be formed.

To achieve the object set forth above, the third aspect of the invention relates to a method for continuously making a plurality of pull-on disposable wearing articles comprising the steps of feeding a web defined by inner and outer surfaces and first and second side edges extending in parallel to each other in a machine direction in the machine direction, folding the web in two along a cross direction being orthogonal to the machine direction in the course of feeding the web so that the first and second side edges may fall into line, then severing the web along cut lines extending in the cross direction to form segments of the web each having a given dimension in the machine direction, and releasably bonding two layers defined by each of the web segments folded in two in the vicinity of transversely opposite side edges of the respective layers extending in parallel to the cut lines in the cross direction by means of fastener means to obtain a plurality of the pull-on disposable wearing articles each having a waist-hole and a pair of leg-holes so that these pull-on disposable wearing articles are successively arranged side by side in the machine direction.

The method for making such wearing articles according to the third aspect of this invention further comprises the steps as follows:

a. forming the web being fed in the machine direction with an annular notch bisected in the machine direction by a region in which the cut line is to be formed and cutting a region extending inside the annular notch away from the web;

b. attaching a pair of first fastener means on an outer surface of the web adjacent to the first side edge as viewed in the cross direction and on both sides, as viewed in the machine direction, of a region in which the cut line is to be formed;

c. forming the web between the region in which the cut line is to be formed and the respective first fastener means with a pair of rectilinear slits extending in the cross direction beyond opposite ends of the first fastener means as viewed in the cross direction but not extending to the first side edge as well as to the annular notch and opposed to each other about the region in which the cut line is to be formed;

d. attaching a fastener's base sheet piece having a pair of second fastener means extending in the machine direction across a pair of the rectilinear slits, respectively, and adapted to be releasably engaged with the first fastener means formed on the both sides of the region to the web through engagement of respective the second fastener means with respective the first fastener means;

e. forming the web on the both sides of the region in which the cut line is to be formed with, in addition to first substantially arc notches on the both sides each having a bottom intersecting the rectilinear slits at ends thereof in the vicinity of the first side edge and its tops extending to the first side edge, second substantially arc notches defined by an inverted shape of the first substantially arc notches, each having a bottom intersecting the rectilinear slits at ends thereof in vicinity of the second side edge and extending to the annular notch;

f. folding the web with the inner surface inside so that the first side edge and the second side edge fall into line while a region of the web surrounded by a pair of the rectilinear slits formed on the both sides of the region in which the cut line is to be formed, the annular notch, the first arc notches and the second arc notch is cut away or retained;

g. bonding, between the region in which the cut line is to be formed and a pair of the rectilinear slits, respectively, a region of the web having been folded in two located aside toward the second side edge to the fastener's base sheet piece directly or indirectly through the intermediary of the surrounded region having been retained in the step f; and h. severing, after the step g, the web together with the fastener's base sheet pieces along the region in which the cut line is to be formed.

According to one preferred embodiment (6) of the third aspect of the invention, the method includes a step of attaching a bodily fluid absorbent member comprising an assembly of bodily fluid absorbent materials and a liquid-pervious sheet at least partially covering a surface of the assembly to the inner surface of the web.

According to another preferred embodiment (7) of the third aspect of the invention, prior to formation of the rectilinear slits, elastic members extending in the machine direction are attached in stretched state to the web in vicinity of the first side edge.

According to still another preferred embodiment (8) of the third aspect of the invention, prior to formation of the annular notch, elastic members are attached in stretched state to the web along a region in which the annular notch is to be formed.

According to the invention defined by the first aspect of the invention, in the step preceding the step of cutting the region surrounded at least by a pair of the rectilinear slits and the notches intersecting a pair of the rectilinear slits away from the web being running in the machine direction, the second fastener means supported on the fastener's base sheet pieces are engaged with the respective first fastener means to attach these fastener's base sheet pieces to the web. In this way, the region of the web extending along the first side edge is free from any significant distortion and there is no apprehension that the shapes of the continuously output wearing articles might become random even if the web having the surrounded regions cut away is fed under a tensile force in the machine direction.

According to the invention defined by the second aspect of the invention also, in the step preceding the step of cutting the region surrounded by the first side edge of the web, the respective rectilinear slits, the annular notch and the respective arc notches away from the web being running in the machine direction, the second fastener means supported on the fastener's base sheet pieces are engaged with the respective first fastener means to attach these fastener's base sheet pieces to the web. In this way, the region of the web extending along the first side edge is free from any significant distortion and there is no apprehension that the shapes of the continuously output wearing articles might become random even if the web having the surrounded regions cut away is fed under a tensile force in the machine direction.

According to the invention defined by the third aspect of the invention also, in the step preceding the step of cutting the region surrounded by the first side edge of the web, the rectilinear slits, the annular notch, the respective first arc notches and the respective second arc notches away from the web being running in the machine direction, the second fastener means supported on the fastener's base sheet pieces are engaged with are engaged with the respective first fastener means to attach these fastener's base sheet pieces to the web. the region of the web extending along the first side edge is free from any significant distortion and there is no anxiety that the shapes of the continuously output wearing articles might become random even if the web having the surrounded regions cut away is fed under a tensile force in the machine direction.

According to the respective preferred embodiments of the first, second and third aspects of the invention, respectively, the wearing article of each aspect of the invention may be provided with bodily fluid absorbent panels, respectively.

According to the respective preferred embodiments (2), (4), (7) of the first, second and third aspects of the invention, the elastic members extending in the machine direction may be attached in stretched state to the web in the vicinity of the first side edge so that these elastic members may serve as the waist elastic members for the wearing articles.

According to the respective preferred embodiments (5), (8) of the second and third aspects of the invention, the elastic members are attached in stretched state to the web destined to form the wearing article along the annular notch so that these elastic members may serve as the leg elastic members for the wearing articles.

DETAILED DESCRIPTION OF THE PREFERRED EMBODIMENTS

Details of a method according to this invention for making a pull-on disposable wearing article will be more fully understood from the description given hereunder with reference to the accompanying drawings.

Figure 1:
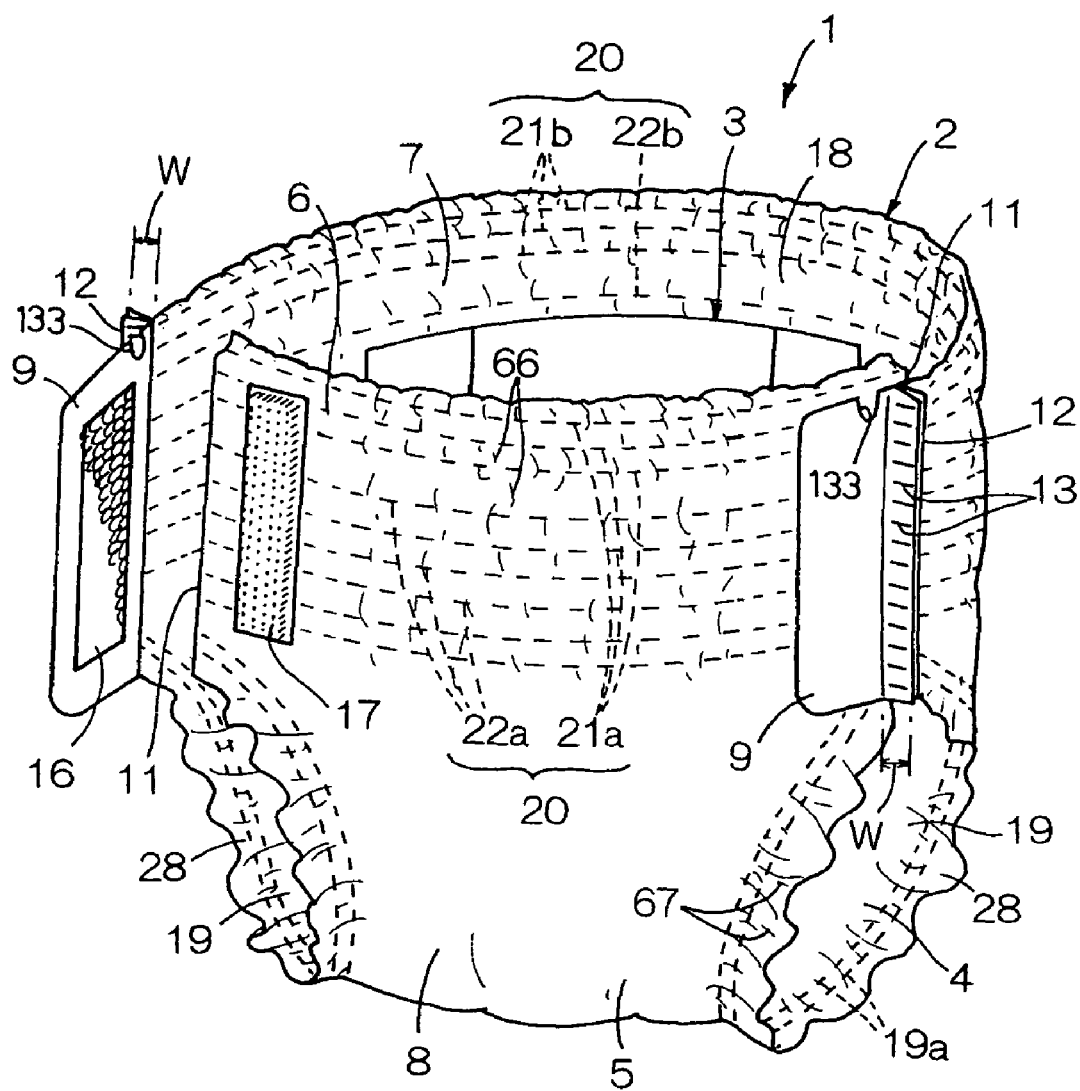
FIG. 1 is a perspective view showing a pull-on diaper.

A pull-on disposable diaper 1 shown in FIG. 1 in a perspective view is the diaper made by a method according to this invention, comprising a body cover 2 and a bodily fluid absorbent panel 3. The body cover 2 has a crotch region 8, a front waist region 6 extending forward from the crotch region 8 and a rear waist region 7 extending rearward from the crotch region 8. These regions 6, 7, 8 are defined by an outer sheet 5 facing the wearer's garment (not shown) and an inner sheet 4 laid inside the outer sheet 5 and facing the wearer's skin (not shown). In the vicinity of transversely opposite side edges 12, 12, flaps 9 formed from sheets provided separately of the inner and outer sheets 4, 5 are bonded to the rear waist region 7 at a plurality of spots 13 arranged intermittently in a vertical direction as viewed in FIG. 1 by use of adhesive or welding technique. Each of the flaps 9 is provided on its inner surface with a loop member 16 constituting a part of a mechanical fastener commercially referred to as MAGIC TAPE attached thereto by use of adhesive or welding technique. In the vicinity of the transversely opposite side edges 11, the front waist region 6 is provided with hook members 17 constituting a counterpart of the mechanical fastener attached thereto by use of adhesive or welding technique. The loop member 16 and the hook member 17 are overlapped together in mutual engagement and thereby the front and rear waist regions 6, 7 are detachably connected with each other in the vicinity of the transversely opposite side edges 11, 12 of the respective waist regions 6, 7. For better understanding of this arrangement, the front and rear waist regions 6, 7 are illustrated to be not connected with each other at the left hand of FIG. 1 and to be connected with each other at the right hand of FIG. 1. When these front and rear waist regions 6, 7 are connected with each other at both the left hand and the right hand of FIG. 1, the diaper 1 is formed with a waist-hole 18 and a pair of leg-holes 19. The waist-hole 18 is provided with waist elastic members 20 extending in a circumferential direction of the waist-hole 18 and each of the leg-holes 19 is provided with a leg elastic member 19a in a circumferential direction of this leg-hole 19. The body cover 2 illustrated herein is formed with a plurality of gathers 66, 67 undulating in the respective circumferential direction as these elastic members 20, 19a contract.

Figure 2:
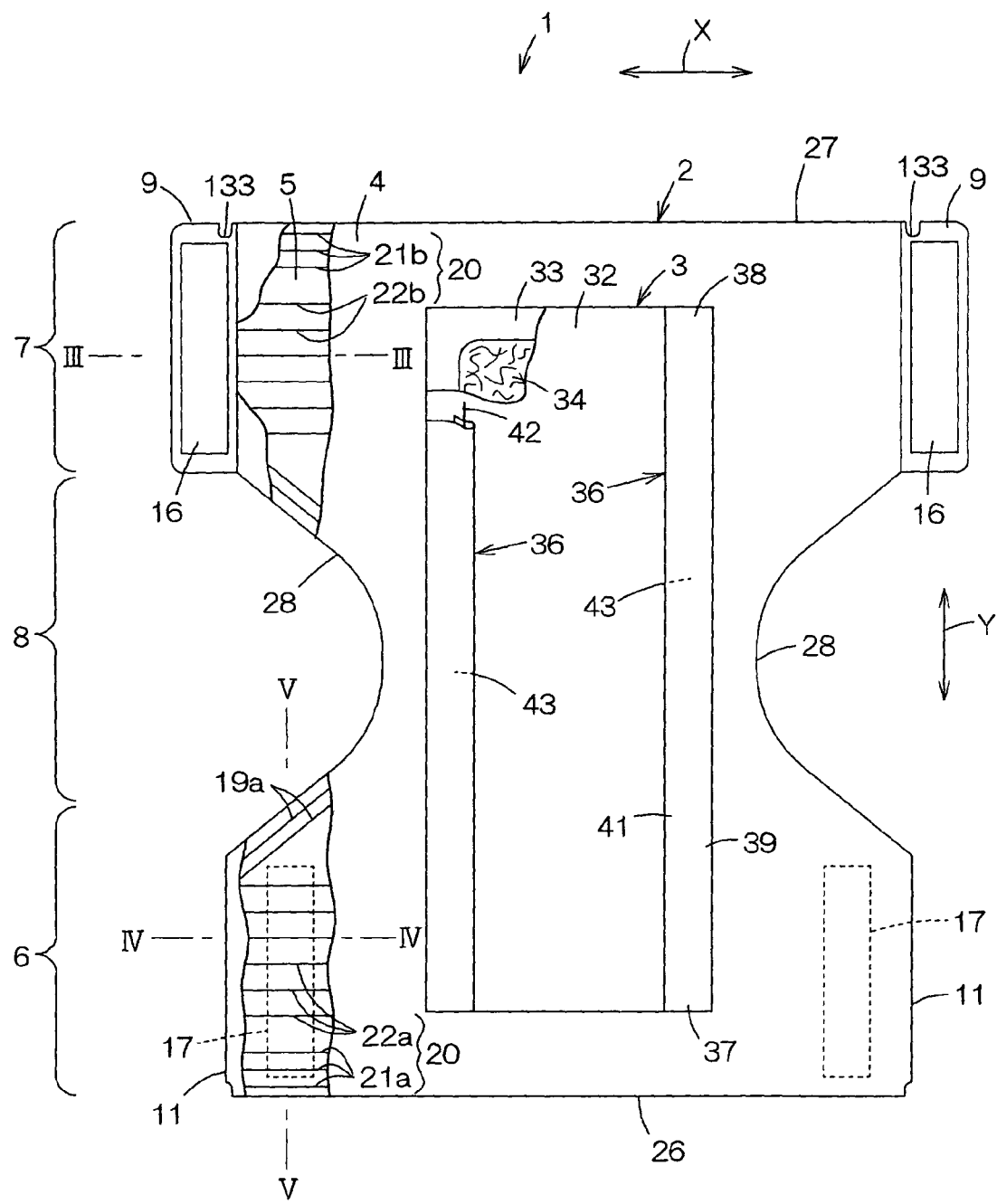
FIG. 2 is a developed view showing the pull-on diaper as partially broken away.

FIG. 2 is a plan view showing the diaper 1 of FIG. 1 with the front and rear waist regions 6, 7 as well as the crotch region 8 having been flattened, partially broken away. In FIG. 2, the front and rear waist regions 6, 7 are in disconnected states, the leg elastic members 19a as well as the waist elastic members 20 are in stretched states and therefore the gathers 66, 67 in FIG. 1 disappear. The diaper 1 has a transverse direction indicated by a double-headed arrow X, a back-and-forth direction indicated by a double-headed arrow Y which is orthogonal to the direction indicated by the double-headed arrow X. The transverse direction X corresponds to the circumferential direction of the diaper 1. In the body cover 2, a dimension between the transversely opposite side edges 11, 11 of the front waist region 6 is slightly smaller than a dimension between the transversely opposite side edges 12, 12 (See FIG. 1) and a difference between these two dimensions is substantially same as a dimension W over which each of the flaps 9 is attached to the rear waist region 7. The front waist region 6 as well as the rear waist region 7 have front and rear ends 26, 27 extending in the transverse direction X and the crotch region 8 has transversely opposite side edges 28 bowing so as to be convex inwardly of the body cover 2. The waist elastic members 20 comprise at least one first elastic member 21a and at least one first elastic member 21b which are provided in the vicinity of the front end 26 and the rear end 27 and extending between the transversely opposite side edges 11, 11 and between the transversely opposite side edges 12, 12 in stretched states, respectively. The waist elastic members 20 further comprise at least one second elastic member 22a and at least one second elastic member 22b lying below the first elastic members 21a, 21b and above the crotch region 8 as viewed in FIG. 1. The second elastic member 22a extends in stretched state between the transversely opposite side edges 11, 11 and the second elastic member 22b extends in stretched state between the transversely opposite side edges 12, 12. Preferably, the first elastic members 21a, 21b are adapted to be pressed against the wearer's waist more tightly than the second elastic members 22a, 22b and, to achieve this, the first elastic members 21a, 21b exhibiting a tensile stress higher than that exhibited by the second elastic members 22a, 22b may be used as the respective first elastic members 21a, 21b. The body cover 2 is further provided along transversely opposite side edges 28 of the crotch region 8 with the leg elastic members 19a attached thereto in stretched state.

As will be seen in FIG. 2, the bodily fluid absorbent panel 3 comprises a liquid-pervious top sheet 32, a liquid-impervious back sheet 33 and a bodily fluid absorbent core 34 interposed between these two sheets 32, 33. The top- and back sheets 32, 33 extend outward beyond a peripheral edge of the core 34 and these outer extensions are put flat and bonded together by use of adhesive or a welding technique. Such bodily fluid absorbent panel 3 is provided along its transversely opposite side edges with leak-barrier cuffs 36 preferably comprising liquid-impervious sheets, respectively. Each of these leak-barrier cuffs 36 has front and rear ends 37, 38 and an outer lateral section 39 bonded to the top sheet 32 and an inner lateral section 41 left free from the top sheet 32. This inner lateral section 41 is provided with an elastic member 42 extending in the back-and-forth direction Y and attached thereto in stretched state. These leak-barrier cuffs 36 form pockets 43 adapted to receive bodily fluids flowing in the transverse direction X. In the bodily fluid absorbent panel 3, the back sheet 33 is bonded to the inner sheet 4 of the body cover 2 by means of hot melt adhesive (not shown).

Figure 3:
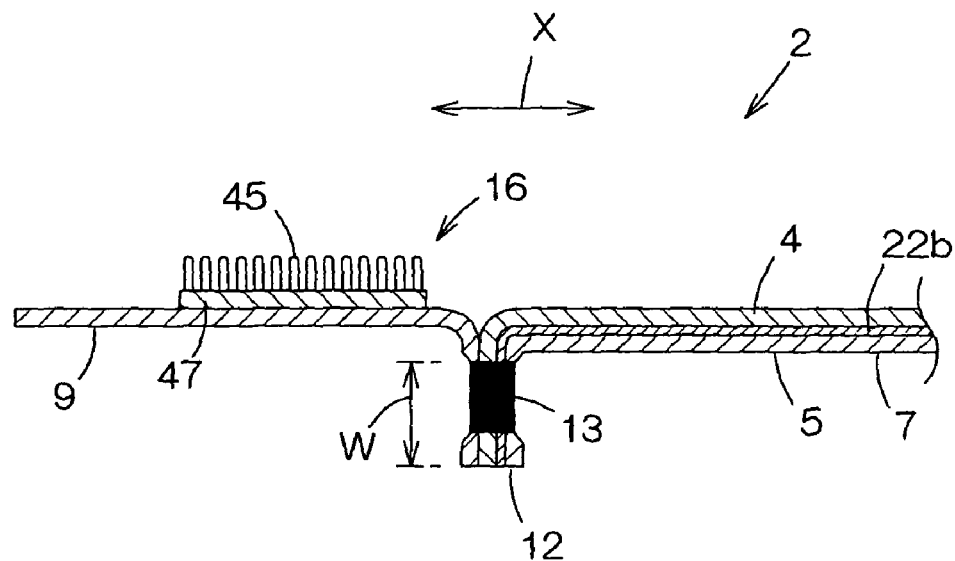
FIG. 3 is a sectional view taken along the line III-III in FIG. 2.

FIG. 3 is a sectional view taken along the line III-III in FIG. 2. The body cover 2 is bonded to the flaps 9 in the vicinity of the side edges 12 of the rear waist region 7 at the spots 13 along respective marginal zones having the width W. In the vicinity of the side edges 12, the first and second elastic members 21b, 22b are intermittently bonded to the inner and outer sheets 4, 5, respectively, by means of hot melt adhesive (not shown) and extend to the spots 13. For simplification, FIG. 3 shows the second elastic member 22b alone. The flaps 9 are firmly bonded to the rear waist region 7 in the vicinity of the side edges 12 thereof so that these flaps 9 should not be peeled off from the rear waist region 7 even when these flaps 9 are pulled in the transverse direction X. The flaps 9 are provided on respective inner surfaces thereof with base sheets 47 bonded thereto and these base sheets 47 are formed on respective inner surfaces with a plurality of loops 45.

In such diaper 1, the inner and outer sheets 4, 5 may be made of nonwoven fabric or plastic film. The top sheet 32 of the bodily fluid absorbent panel 3 may be formed from nonwoven fabric or perforated plastic film and the back sheet 33 may be formed by plastic film. For the core 34, fluff pulp and super-absorbent polymer particles.

Figure 4:
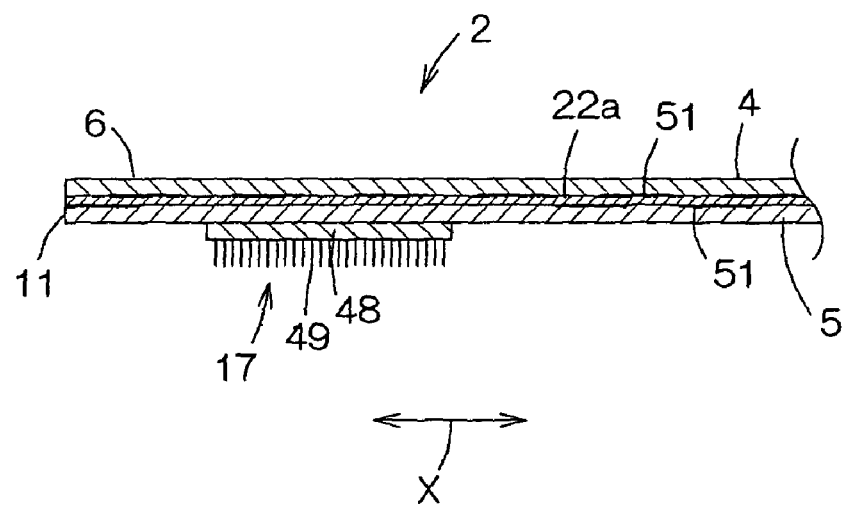
FIG. 4 is a sectional view taken along the line IV-IV in FIG. 2.
Figure 5:
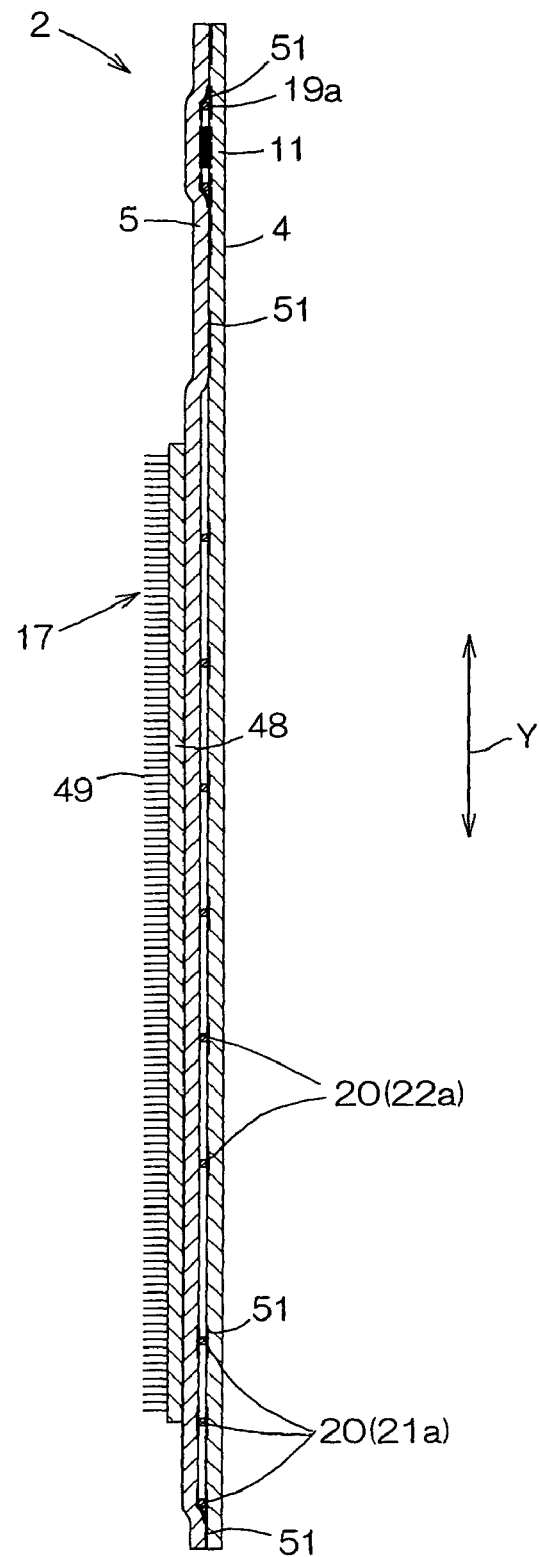
FIG. 5 is a sectional view taken along the line V-V in FIG. 2.

FIG. 4 is a sectional view taken along the line IV-IV in FIG. 2 and FIG. 5 is a sectional view taken along the line V-V in FIG. 2. In the vicinity of the side edges 11 of the front waist region 6, the body cover 2 is provided with the hook members 17 each comprising a base sheet 48 and a plurality of hooks 49 rising on the base sheet 48 wherein each of the base sheets 48 is bonded to the outer surface of the outer sheet 5. Referring to FIG. 4, the inner sheet 4, the outer sheet 5 and the second elastic member 22a are bonded together intermittently in a longitudinal direction of the second elastic member 22a by means of hot holt adhesive 51. Referring to FIG. 5, the outer sheet 5 is bonded to the first elastic member 21a, the leg elastic members 19a and the inner sheet 4 intermittently in the back-and-forth direction Y by means of hot melt adhesive 51.

Figure 6:
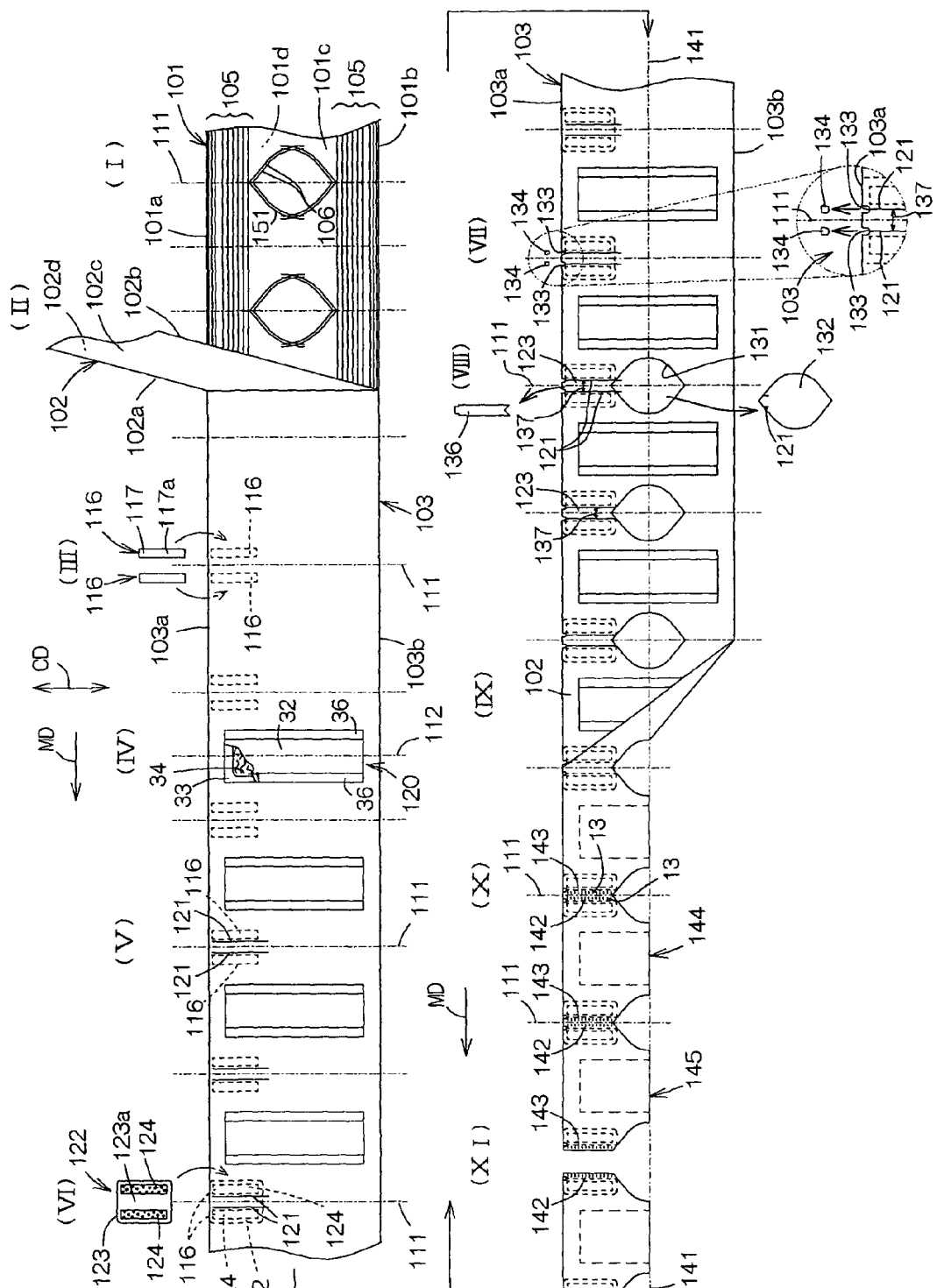
FIG. 6 is a diagram partially illustrating a process according to this invention for continuously making the pull-on diaper.

FIG. 6 is a diagram partially illustrating a process for making the diaper 1 of FIG. 1, wherein a machine direction and a cross direction which is orthogonal to the machine direction are indicated by MD and CD, respectively, and the process is illustrated partially in an enlarged scale. In step I, a first continuous sheet 101 runs in the machine direction MD. The first continuous sheet 101 has first and second side edges 101a, 101b extending in parallel to each other in the machine direction MD, an inner surface 101c appearing in FIG. 6 and an outer surface 101d opposite thereto. The first continuous sheet 101 includes a plurality of thread-like first elastic members 105 attached in stretched state to the inner surface 101c in the vicinity of the first and second side edges 101a, 101b. The first continuous sheet 101 is further provided in an intermediate section defined between the first and second side edges 101a, 101b with a plurality of thread-like second elastic members 106 attached in stretched state thereto so as to define an annulus 151. The first continuous sheet 101 is intermittently formed with a plurality of the thread-like second elastic members 106 at regular intervals in the machine direction MD.

In step II, a second continuous sheet 102 with a substantially same width as that of the first continuous sheet 101, first and second side edges 102a, 102b, an inner surface 102c and an outer surface 102d opposite to the inner surface 102c is continuously fed with the inner surface 102c facing upward in the machine direction MD and the outer surface 102d is bonded to the inner surface 101c of the first continuous sheet 101 to form first composite sheet 103. The outer surface 102d and the inner surface 101c are preferably bonded to each other intermittently both in the machine direction MD and in the cross direction CD. The first composite sheet 103 has first side edge 103a along which the first side edge 101a of the first continuous sheet 101 is placed on the first side edge 102a of the second continuous sheet 102 substantially in alignment with each other and second side edge 103b along which the second side edge 101b of the first continuous sheet 101 is placed on the second side edge 102b of the second continuous sheet 102 substantially in alignment with each other. Imaginary lines 111 extending across the first continuous sheet 101 in step I and across the first composite sheet 103 in the subsequent steps correspond to first center lines bisecting the respective annuli 151 in the machine direction MD and imaginary lines 112 correspond to second center lines bisecting a dimension defined between each pair of the adjacent annuli 151, 151 in the machine direction MD. The first center line 111 corresponding also to cut line in step XI described hereinafter.

In step III, a pair of hook members 116 are attached to the outer surface 101d of the first continuous sheet 101 constituting the first composite sheet 103 in the vicinity of the first center line 111 so as to be symmetric about the first center line 111. These hook members 116 are destined to become the hook members 17 in FIGS. 1 and 4, each comprising first base sheet 117 and hooks (not shown) rising on the outer surface (not shown) of the first base sheet 117. The first base sheet 117 has inner surface 117a opposite to the outer surface attached to the first continuous sheet 101.

In step IV, a bodily fluid absorbent member 120 is attached to the inner surface 102c of the second continuous sheet 102 constituting the first composite sheet 103 by means of hot melt adhesive (not shown) so that a transverse center line (not shown) and the second center line 112 may fall into line. The bodily fluid absorbent member 120 is destined to become the bodily fluid absorbent panel 3 of FIG. 2 and comprises the bodily fluid absorbent cores 34 each formed by assembly of bodily fluid absorbent materials, the liquid-pervious top sheet 32 covering at least the inner surface of the cores 34, the liquid-impervious back sheet 33 covering the outer surface of the cores 34 and respective pairs of the leak-barrier cuffs 36.

In step V, on the first composite sheet 103 a linear slit 121 extending in the cross direction CD through the first composite sheet 103 is formed between the first center line 111 and the hook member 116 adjacent to this first center line 111. The slit 121 extends beyond opposite ends in the cross direction CD of the hook member 116 but neither to the first side edge 103a nor the second side edge 103b.

In step VI, each of loop members 122 is releasable attached to each pair of the adjacent hook members 116, 116 so as to extend across the first center line 111 lying between these adjacent hook members 116, 116. The loop member 122 comprises a base sheet 123 and a pair of loop arrays 124 formed on the inner surface 123a of the base sheet 123. Each pair of the loop arrays 124 are spaced apart from each other in the machine direction MD by a substantially same distance as a distance by which the pair of the hook members 116 adapted to be anchored on the above-mentioned pair of the loop arrays 124. Each of the loop arrays 124 has dimensions as measured in the machine direction MD and in the cross direction CD are substantially same as or slightly larger than dimensions of the hook member 116 as measured in the machine direction MD and in the cross direction CD. The base sheet 123 is formed from a sheet piece made of nonwoven fabric or plastic film having sufficient dimensions as measured in the machine direction MD and in the cross direction CD.

In step VII, the first composite sheet 103 is formed with substantially arc notches 133 in the vicinity of the first side edge 103a. Each of these arc notches 133 is described by the notch 133 having top ends which intersect the first side edge 103a and a bottom which intersects ends of the slit 121 put aside toward the first side edge 103a. By forming these notches 133, the arc notch pieces 134 are removed from the first composite sheet 103. Details of these notches 133 and arc notch pieces 134 will be more fully understood from a scale-enlarged diagram showing a circled part of the first composite sheet 103. In the diaper 1 shown by FIGS. 1 and 2, these notches 133 appear in the flaps 9.

In step VIII, an annular notch 131 extending across the first center line 111 and being symmetric about this first center line 111 is formed. The annular notch 131 intersects a pair of slits 121 opposed to each other symmetrically about the first center line 111 at respective ends of these two slits 121 put aside toward the second side edge 103b. A region surrounded by the annular notch 131 is cut away as a disc form sheet piece 132 and a region surrounded by the first side edge 103a, a pair of the slits 121, the annular notch 131 and a pair of the arc notch 133 is cut away as a sheet piece 136 to form a gap 137 on the first composite sheet 103. It should be noted here that the base sheet 123 for the loop member 122 having previously been attached to the first composite sheet 103 is exposed in this gap 137.

In step IX, the first composite sheet 103 is folded in two along a third center line 141 bisecting the width of the first composite sheet 103 with the second continuous sheet 102 lying inside and with the first and second side edges 103a, 103b placed upon each other.

In step X, the second continuous sheet 102 faces the base sheet 123 of the loop member 122 in the gap 137 so that first and second bonding regions 142, 143 extending in the cross direction CD may be formed on both sides of the first center line 111 as viewed in the machine direction MD. In these bonding regions 142, 143, the second continuous sheet 102 is bonded to the base sheet 123 to form a second composite sheet 144. In the second composite sheet 144, the first bonding region 142 and the second bonding region 143 are identical to each other so far as the construction is concerned but the first bonding region 142 is formed ahead of the first center line 111 and the second bonding region 143 is formed behind this first center line 111 as viewed in the machine direction MD. In the diagram, these first and second bonding regions 142, 143 are respectively illustrated as aggregates of a plurality of the bonding spots 13 (See FIG. 1) arranged intermittently in the cross direction CD.

In step XI, the second composite sheet 144 is severed together with the respective base sheets 123 along cut lines defined by the respective first center lines 111 successively in the machine direction MD to obtain individual pull-on diapers 1.

Each of the diapers 1 obtained in the step XI is same as the diaper 1 of FIG. 1. More specifically, the first and second continuous sheets 101, 102 are severed into the sheet pieces respectively defining the outer sheet 5 and the inner sheet 4 of the diaper 1 of FIG. 1. The bodily fluid absorbent member 120 defines the bodily fluid absorbent panel 3. The section of the first composite sheet 103 lying above the third center line 141 in the steps VIII, IX and the subsequent steps defines the front waist region 6 and a part of the crotch region 8 while the section of the first composite sheet 103 lying below the third center line 141 in these steps defines the rear waist region 7 and the remaining part of the crotch region 8. The hook member 116 defines the hook member 17 of the diaper 1 shown in FIG. 1, the base sheet 123 of the loop member 122 is severed along the first center line 111 to define the flaps 9 on both sides of this first center line 111 and each of the loop arrays 124 defines the loop member 16. The flaps 9 are attached to the rear waist region 7 at the bonding spots 13 of the first and second bonding regions 142, 143. The slits 121 of the first composite sheet 103 defines the side edges 11 of the front waist region 6 in FIG. 1 and the second composite sheet 144 is severed along the first center lines 111 to form the side edges 12 in FIG. 1. The front waist region 6 and the rear waist region 7 are detachably connected with each other by means of the flaps 9 in the vicinity of the side edges 11 and in the vicinity of the side edges 12. The annular notch 131 formed on the first composite sheet 103 defines the side edges 28 of the crotch region 8. A plurality of the first elastic members 105 define the elastic members 21a, 21b and 22a, 22b but it should be noted that the number of these elastic members 105 as well as the spacing of these elastic members 105 in the cross direction CD are not specified. The second elastic members 106 define the leg elastic members 19a but it should be noted that the number of these elastic members 106 as well as the shape of the annulus 51 are not specified. While FIG. 1 shows the diaper 1 with one of the flags 9 bonded to the front waist region 6 and the other not bonded to the front waist region 6, FIG. 6 illustrates the both flaps 9 bonded to the front waist region 6.

In the step illustrated in FIG. 6, the first composite sheet 103 running in the machine direction MD is subjected to a tensile force functioning to drive the sheet 103 in the machine direction MD. While the gap 137 extending from the first side edge 103a to the annular notch 131 is formed on the first composite sheet 103, in the step VIII, the base sheet 123 of the loop member 122 has been previously attached on the first composite sheet 103 in such a manner that the base sheet 123 extends in the machine direction MD so as to extend across the gap 137. The tensile force functioning to drive this first composite sheet 103 in the machine direction MD is not substantially affected by the presence of the gap 137. Specifically, the tensile force can evenly exert on the first composite sheet 103 along the first side edge 103a also behind each of the gaps 137 (toward the right hand as viewed in FIG. 6). In addition, the presence of the base sheet 123 attached to the first composite sheet 103 so as to extend across the gap 137 serves to restrain contraction of the elastic members 105. Consequentially, the first composite sheet 103 is evenly subjected to the tensile force along the first and second side edges 103a, 103b without an anxiety that the front and rear waist regions 6, 7 of the individual diaper 1 might have respective resultant shapes distorted. Also between each pair of the adjacent individual diapers 1 made in the continuous fashion, it is not apprehended that these waist regions 6, 7 might have random shapes. In the step illustrated in FIG. 6, it is possible to employ well-known conveyer means such as endless belts and nip rolls to run the first and second continuous sheets 101, 102 and the first and second composite sheets 103, 104 in the machine direction MD. It should be noted that when forming the slit 121 into the first composite sheet 103 running in step V, a cutter is disposed with respect to one of upper and lower surfaces of the first composite sheet 103 while an anvil is disposed with respect to the other and thereby movement of the cutter and the anvil in the machine direction MD is synchronized with a running speed of the first composite sheet 103. It is preferable that the anvil is covered by an antislip material such as "TESA TAPE 4863 or 4563" (Trademark) or a suction apparatus is provided so as to function on the web and the antislip material or the suction apparatus prevents the first composite sheet 103 from slipping against a surface of the anvil when the cutter acts on the first composite sheet 103. The surface of the anvil may be treated with a suitable agent having a high antislip effect instead of the foregoing antislip material.

In the step illustrated in FIG. 6, the sub-step of forming the arc notch 133 and the sub-step of forming the annular notch 131 may be sequentially inversed. It is possible to attach the bodily fluid absorbent member 120 to the first composite sheet 103 in any step other than the step IV. The sheet piece 136 having been described above to be cut away from the first composite sheet 103 in the step VIII may be previously bonded to the base sheet 123, for example, by means of adhesive and thereby be left in the gap 137 without cutting away from the first composite sheet 103. By means of this sheet piece 136 left in the gap 137, the second continuous sheet 102 and the base sheet 123 may be indirectly bonded to each other in the step X.

Figure 7:
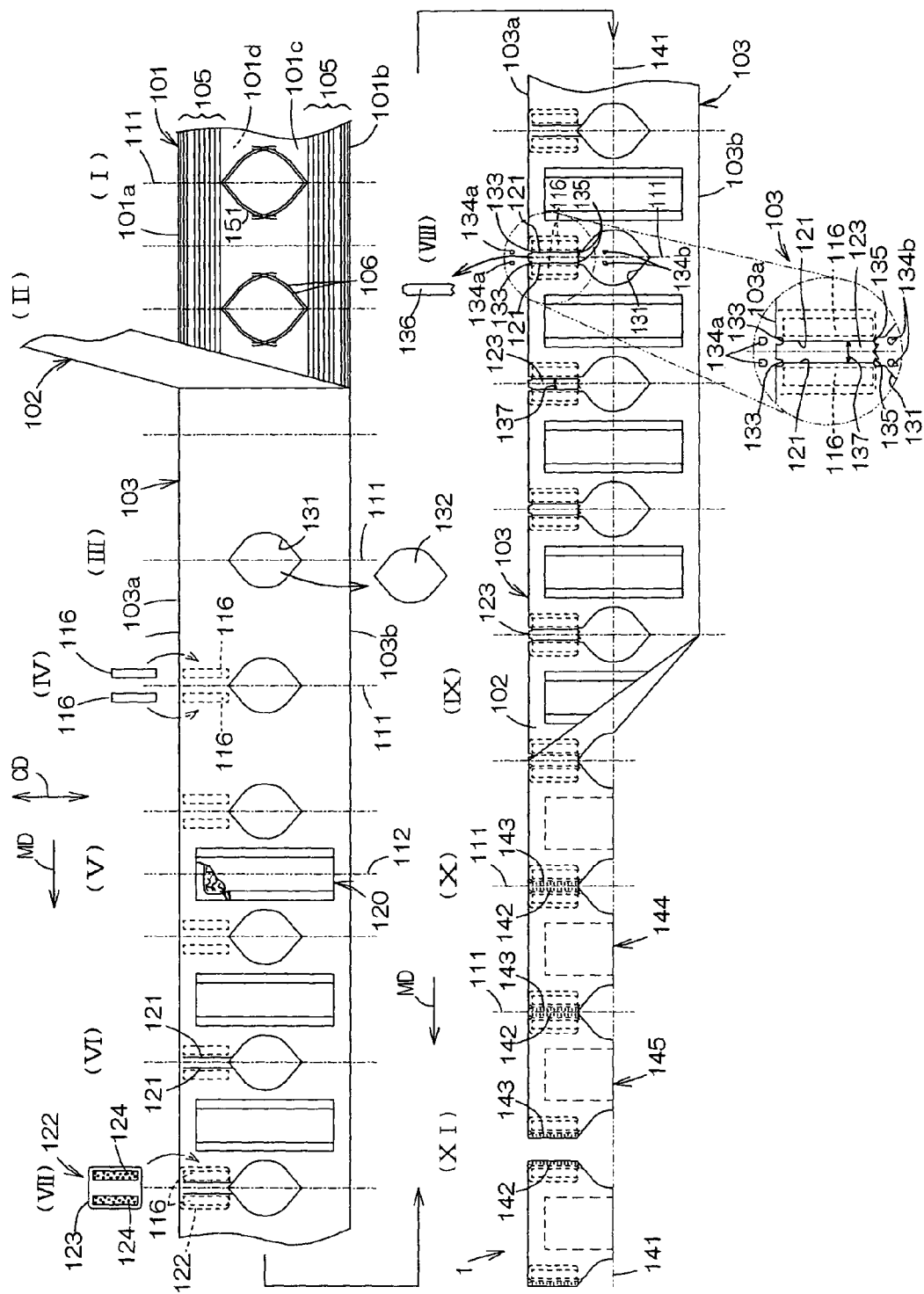
FIG. 7 is a diagram similar to FIG. 6, illustrating one preferred embodiment of this invention.

FIG. 7 is a diagram similar to FIG. 6, partially illustrating the process according to one preferred embodiment of this invention. According to this embodiment, the first continuous sheet 101 and the second continuous sheet 102 are bonded to each other in the step II to form the first composite sheet 103. In the step III, the annular notch 131 which is symmetric about the first center line 111 and the annular sheet piece 132 is cut away from the first composite sheet 103.

In step IV, the hook members 116 are attached to the first composite sheet 103 in the same manner as in the step III illustrated in FIG. 6.

In step V, the bodily fluid absorbent member 120 illustrated partially broken away is attached to the first composite sheet 103 so that a transverse center line and the second center line 112 may fall into line in the same manner as in the step IV illustrated in FIG. 6.

In step VI, the slits 121 are formed on both sides of the first center line 111 in the same manner as in the step V illustrated in FIG. 6. The slit 121 extends beyond opposite ends in the cross direction CD of the hook member 116 but neither to the first side edge 103a nor the annular notch 131 of the first composite sheet 103.

In step VII, a pair of the loop arrays 124 of the loop member 122 are releasable engaged with the respective hook members 116 lying on both sides of the first center line 111, respectively in the same manner as in the step VI illustrated in FIG. 6.

In step VIII, first arc notches 133 are formed in the same manner as in the step VII illustrated in FIG. 6. Specifically, these first arc notches 133 are defined by substantially intersecting the first side edge 103a and intersecting also the ends of the slits 121 in the vicinity of the first side edge 103a. In addition to these first arc notch 133, second arc notch 135 are formed in the step VIII. Each of the second arc notch 135 is defined by an inverted shape of the first arc notch 133 wherein a bottom of the second arc notch 135 intersects the ends of the slits 121 in the vicinity of the second side edge 103b and tops of arc intersect the annular arc notch 131. Arc notch pieces 134a, arc notch pieces 134b are cut away from the first composite sheet 103 and a region surrounded by the first side edge 103a, a pair of the slits 121, the annular notch 131, a pair of arc notch 133 and a pair of the second arc notch 135 is cut away as a notch piece 136. By removal of the notch piece 136, the first composite sheet 103 formed with the gap 137 extending from the first side edge 103a to the annular notch 131. It should be noted that the base sheet 123 of the hook member 116 is exposed in the gap 137. Details of this gap 137 and the other components will be more fully understood from a scale-enlarged diagram showing a circled part of the first composite sheet 103.

In step IX, the first composite sheet 103 is folded in two along a third center line 141 bisecting the width of the first composite sheet 103 with the second continuous sheet 102 lying inside and with the first and second side edges 103a, 103b placed upon each other in the same manner as in the step IX illustrated in FIG. 6.

In step X, in the same manner as in the step X illustrated in FIG. 6, the second continuous sheet 102 faces the base sheet 123 of the loop member 122 in the gap 137 so that first and second bonding regions 142, 143 extending in the cross direction CD may be formed on both sides of the first center line 111 as viewed in the machine direction MD. In these bonding regions 142, 143, the second continuous sheet 102 is bonded to the base sheet 123 to form a second composite sheet 144.

In step XI, the second composite sheet 144 is severed together with the respective base sheets 123 along cut lines defined by the respective first center lines 111 successively in the machine direction MD to obtain individual pull-on diapers 1.

The process illustrated in FIG. 7 is distinguished from the process illustrated in FIG. 6 in that the rectilinear slits 121 are formed after the annular notch 131 has been formed. These slits 121 extend from the inside of the first side edge 103a in the cross direction toward but short of the annular notch 131. A pair of the first arc notches 133 as well as a pair of the second arc notches 135 defined by the inverted shape of the first arc notch 133 are formed on the first composite sheet 103. The region surrounding by the first side edge 103a, a pair of the slits 121, a pair of the first arc notch 133, a pair of the second arc notch 135 and the annular notch 131 is cut away as the notch piece 136 from the first composite sheet 103 so as to form the gap 137. In the step preceding the step VIII in which the gap 137 is formed, the base sheet 123 of the loop member 122 has previously been engaged with the first composite sheet 103 so as to extend across the gap 137. The tensile force functioning to drive such first composite sheet 103 in the machine direction MD is not affected by the presence of the gaps 137 and can evenly exert on the first composite sheet 103 along the first side edge 103a also behind each of the gaps 137 (toward the right hand as viewed in FIG. 7). Consequentially, just like the case illustrated by FIG. 6, the first composite sheet 103 obtained by the process illustrated in FIG. 7 is evenly subjected to the tensile force along the first and second side edges 103a, 103b without an anxiety that the front and rear waist regions 6, 7 of the individual diaper 1 might have respective resultant shapes distorted and/or being random.

Figure 8:
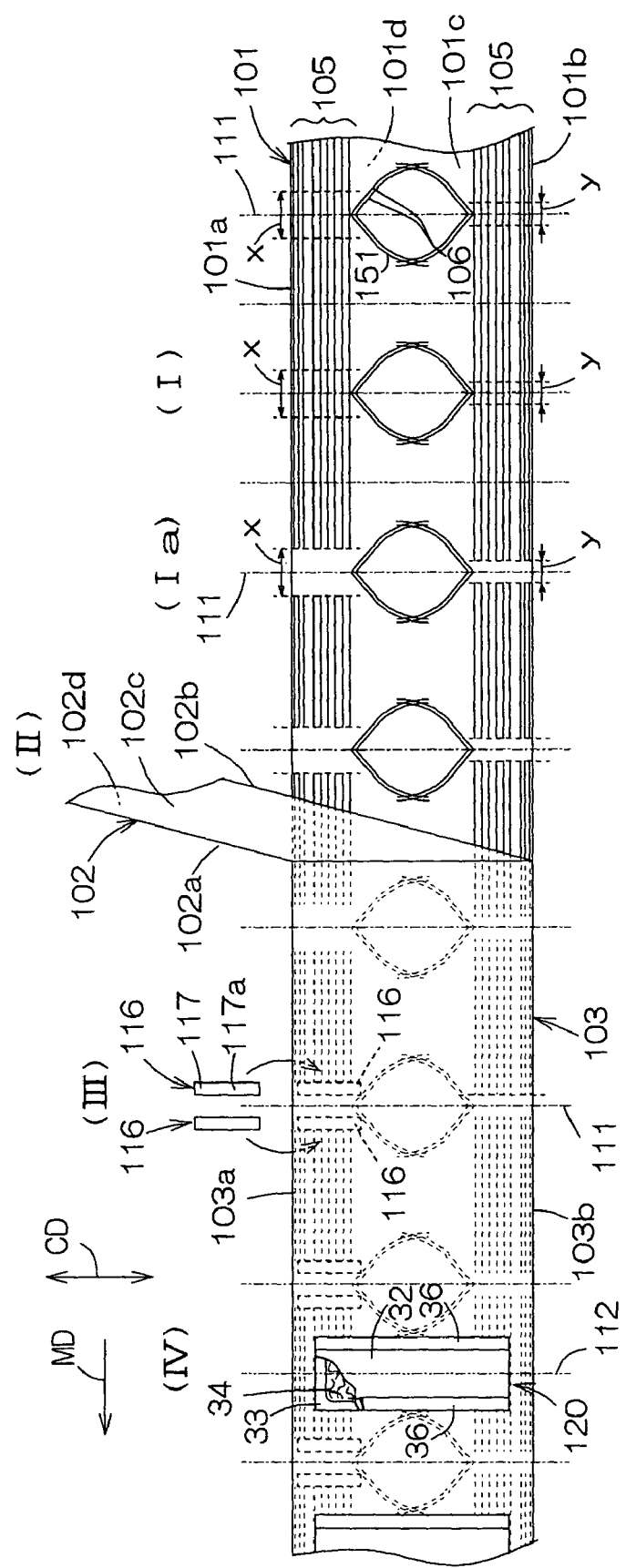
FIG. 8 is a diagram similar to FIG. 6, illustrating another preferred embodiment of this invention.

FIG. 8 is a diagram similar to FIG. 6, partially illustrating the process according to another preferred embodiment of this invention. It should be noted here that in steps III, IV of FIG. 8, the elastic members 105, 106 interposed between the first and second continuous sheets 101, 102 are indicated by imaginary lines. Similarly to the case illustrated in FIG. 6, in step I of FIG. 8, the first continuous sheet 101 is fed in the machine direction MD. In the vicinity of the first side edge 101a and the second side edge 101b, a plurality of the continuous thread-like elastic members 105 are bonded to the inner surface 101c of the first continuous sheet 101 by means of hot melt adhesive (not shown). It should be noted that the elastic members 105 are left free from the first continuous sheet 101 in regions each defined by a width x in the vicinity of the first side edge 101a and regions each defined by a width y in the vicinity of the second side edge 101b.

In step Ia provided between steps I and II in FIG. 8, the elastic members 105 are respectively cut along the first center line 111. As a result, the elastic members 105 located aside toward the first side edge 101a contract in the machine direction MD and face-to-face ends of the elastic members 105 formed by cutting the elastic members 105 in this manner are spaced one from another by the width x about the first center line 111. The elastic members 105 located aside toward the second side edge 101b also contract in the machine direction MD and face-to-face ends of the elastic members 105 formed by cutting the elastic members 105 in this manner are spaced one from another by the width y about the first center line 111.

In step II, similarly to the case illustrated in FIG. 6, the second continuous sheet 102 is fed in the machine direction MD and bonded to the first continuous sheet 101.

In step III, the hook member 116 is attached to the outer surface 101d of the first continuous sheet 101 in a region having the width x and occupied by none of the elastic members 105.

Steps in and after step IV illustrated in FIG. 8 are similar to the steps in and after the step IV illustrated by FIG. 6 except that, in the step of bonding the base sheet 123 to the first composite sheet 103, regions of the first composite sheet 103 each having the width y and occupied by none of the elastic members 105 are bonded to the base sheet 123.

The process illustrated in FIG. 8 effectively sweeps away an apprehension that the elastic members 105 might cause the first continuous sheet 101 and the second continuous sheet 102 to be formed with irregularities and thereby make it difficult to bond the hook member 116 to the first continuous sheet 101 and to bond the base sheet 123 to the second continuous sheet 102. The values of the width x and the width y in the step I maybe appropriately selected to obtain the desired effect. It is possible to modify the process illustrated in FIG. 8 so that the elastic members 105 may be cut along the first center line 111 after the first continuous sheet 101 and the second continuous sheet 102 have been placed upon and bonded to each other.

Figure 9:
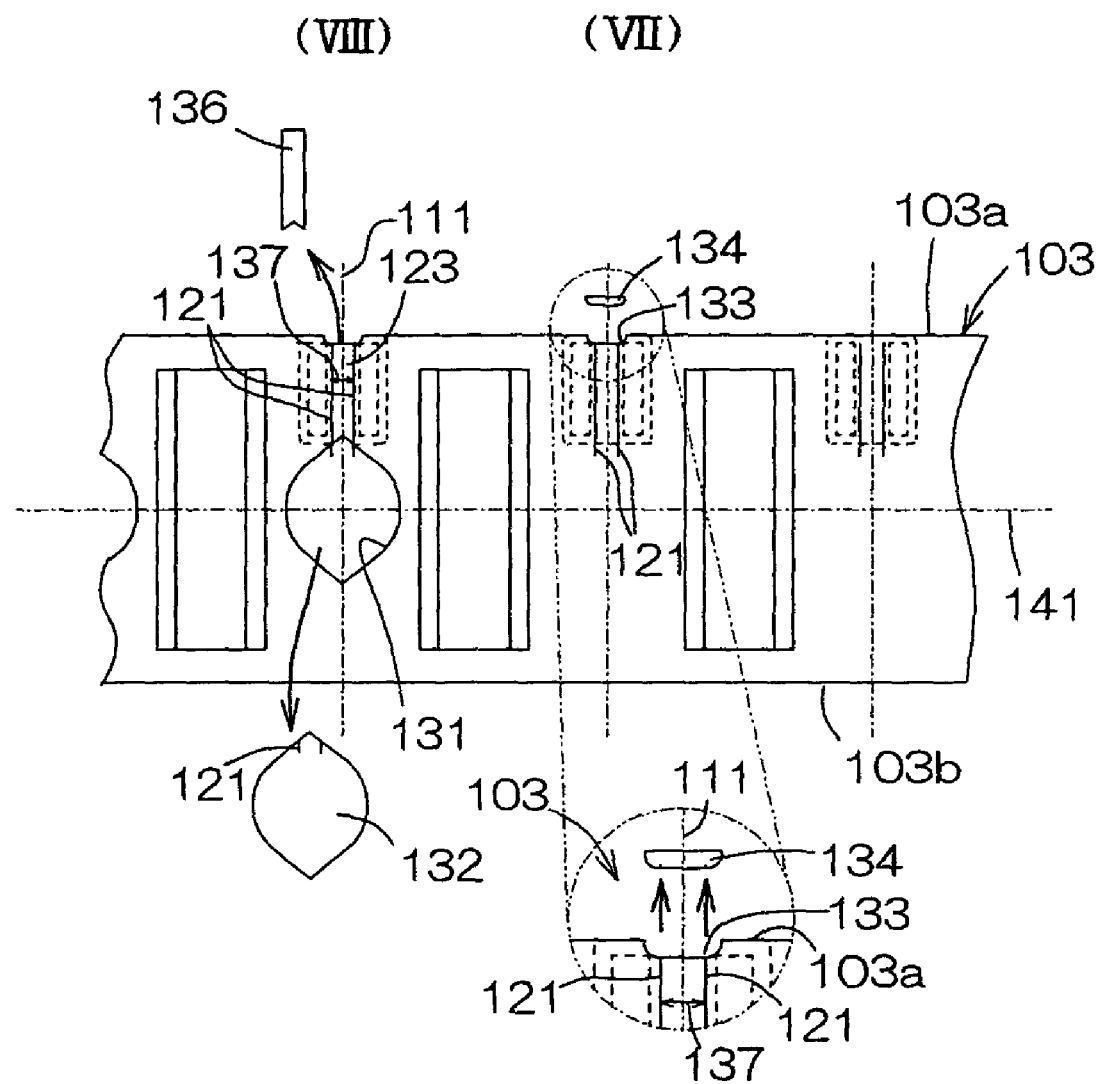
FIG. 9 is a diagram similar to FIG. 6, illustrating still another preferred embodiment of this invention.
Figure 10:
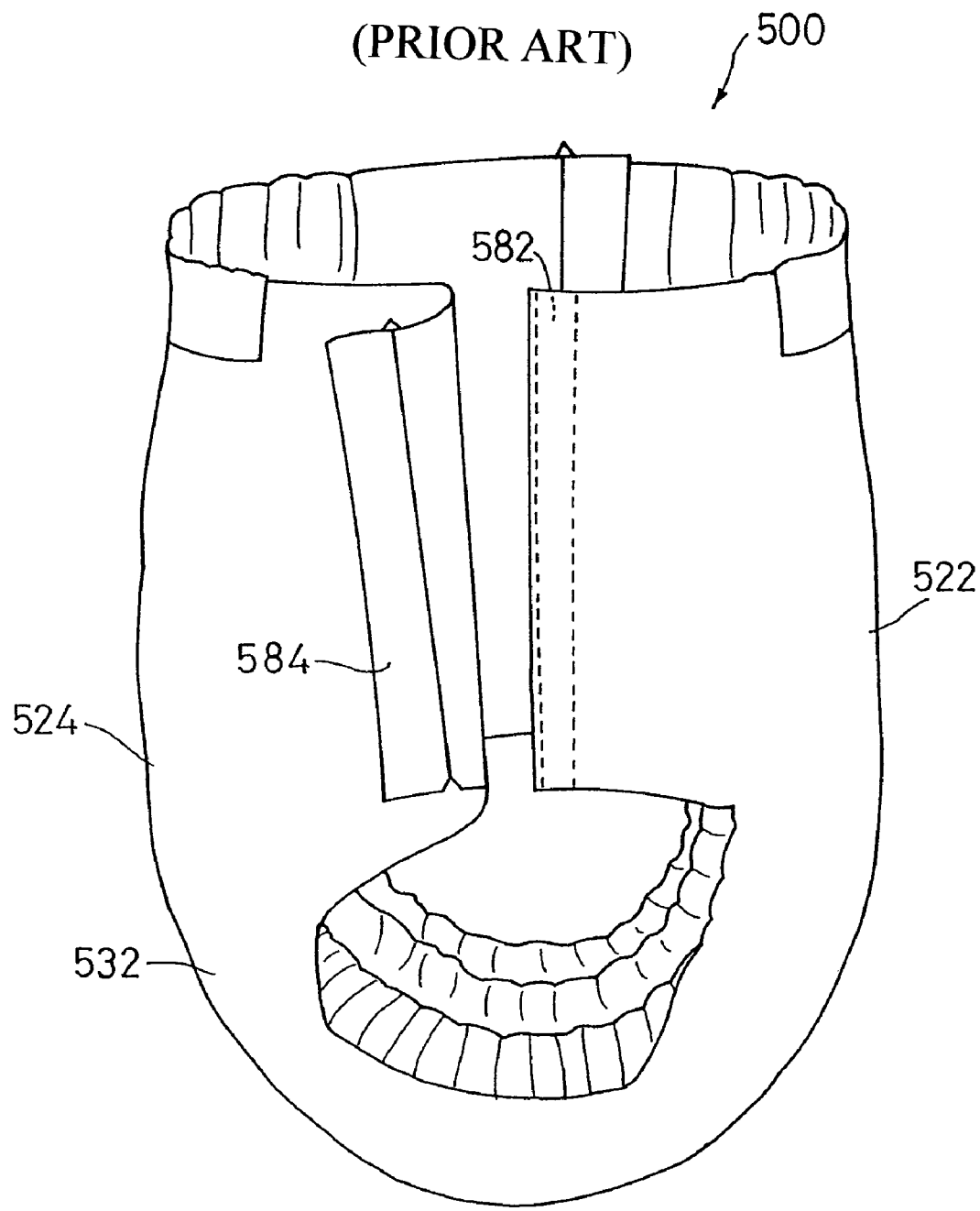
FIG. 10 is a perspective view showing an example of the pull-on wearing article of prior art.
Figure 11:
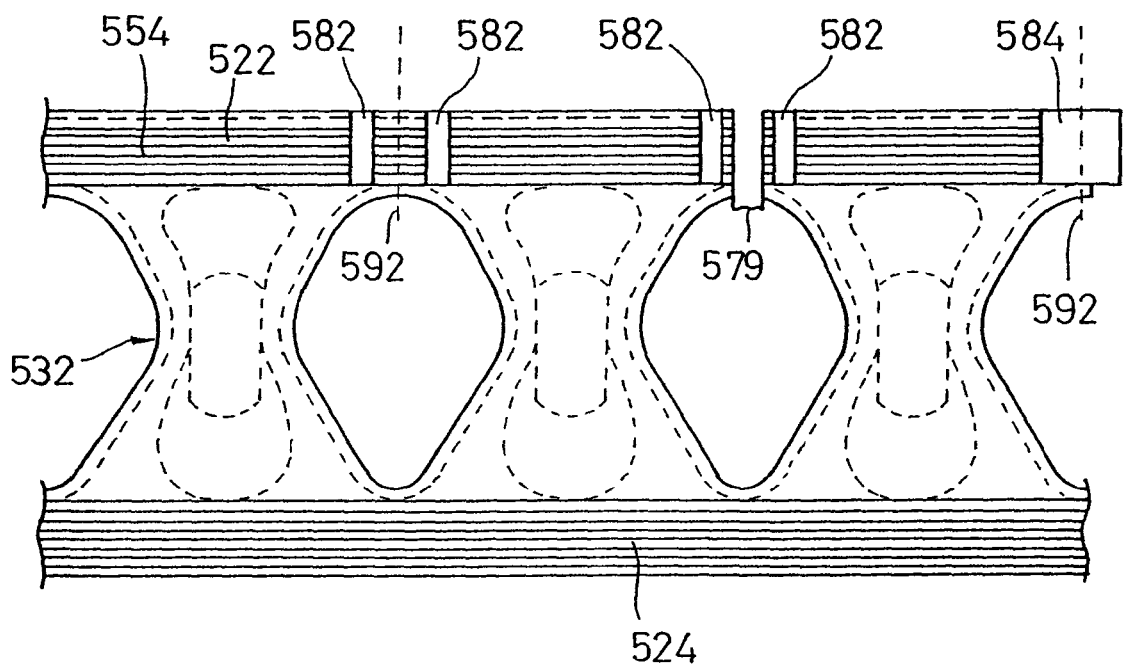
FIG. 11 is a diagram illustrating the process for making the wearing article shown in FIG. 10.

FIG. 9 also is a diagram similar to FIG. 6, partially illustrating the process of this invention according to still another preferred embodiment. In step VII of FIG. 9 corresponding to the step VII of FIG. 6, the first composite sheet 103 is formed with a single arc notch 133 intersecting the first center line 111 and intersecting also a pair of the slits 121 opposed to each other with this first center line 111 lying there between and a single arc notch piece 134 is cut away. In step VIII of FIG. 9 corresponding to the step VIII of FIG. 6, a region surrounded by the single arc notch 133, the annular notch 131 and a pair of the slits 121 is cut away from the first composite sheet 103 as the sheet piece 136 and thereby the gap 137 is formed.

While the method according to this invention for continuously making the pull-on diaper as an typical example of the pull-on wearing article has been described above particularly in reference with FIGS. 6 and 7 wherein the web fed in the machine direction MD comprises the first composite sheet 103 consisting of the first continuous sheet 101 and the second continuous sheet 102, this invention may be implemented in the other various manners. For example, such web may be replaced by web comprising any one of the first continuous sheet 101 and the second continuous sheet 102 or replaced by web comprising, in addition to the first continuous sheet 101 and the second continuous sheet 102, third continuous sheet. Furthermore, the invention maybe implemented without attaching the first elastic members 105 and the second elastic members 106 to any one of these web component sheets. The annular notch 131 illustrated to be substantially symmetric about the third center line 141 in FIGS. 6 and 7 may be replaced by the annular notch 131 which is asymmetric about the third center line 141. The arrangement such that the loop members 16 are releasable engaged with the hook members 17 attached to the front waist region 6 may be replaced by the arrangement such that the loop members 16 attached to the flaps extending from the front waist region 6 toward the rear waist region 7 are releasable engaged with the hook members 17 attached to the rear waist region 7. In other words, the upper half region of the first composite sheet 103 lying above the third center line 141 in FIGS. 6 and 7 may be destined to become either the front waist region 6 or the rear waist region 7 of the diaper 1. In the illustrated embodiments, the loop member 16 may be replaced by the hook member 17 while the hook member 17 may be replaced by the loop member 16. In addition, the fastener used to connect the front and rear waist regions 6, 7 with each other is not limited to so-called mechanical fastener consisting of the loop member 16 and the hook member 17. For example, any one of the loop member 16 and the hook member 17 may be replaced by pressure-sensitive adhesive zones formed by coating any one of the front and rear waist regions 6, 7 and the flaps 9 and the other may be replaced by target zone(s) to which the pressure-sensitive adhesive zones are detachably anchored.

This invention having been described with respect to the pull-on disposable diaper 1 as the typical embodiment is applicable also to the other pull-on wearing article such as incontinence pants and training pants. Depending on particular applications of these wearing articles, the configuration of the bodily fluid absorbent member 120 in the illustrated embodiment may be appropriately modified and even it is possible to do without use of the bodily fluid absorbent member 120.

This invention enables the pull-on disposable wearing article to be continuously produced without the apprehension that the front and rear waist regions might respectively have shapes distorted and/or being random in each of the individual diapers as well as between each pair of the adjacent individual diapers.

The entire discloses of Japanese patent Application Nos. 2004-251952 and 2005-202431 filed on Aug. 31, 2004 and Jul. 12, 2005, respectively, including specification, drawings and abstract are herein incorporated by reference in its entirety.

What is claimed is:

1. A method of continuously making pull-on disposable wearing articles, said method comprising:

feeding a web in a machine direction, said web having opposite first and second surfaces and opposite first and second side edges that extend in said machine direction, folding said web in two in a cross direction orthogonal to said machine direction while feeding said web, and severing said folded web along cut lines, which extend in said cross direction, into individual pull-on disposable wearing articles each having a waist-hole and a pair of leg-holes so that these pull-on disposable wearing articles are successively arranged side by side in said machine direction, said method further comprising:

attaching a pair of first fastener elements to the first surface of said web on opposite sides, as viewed in said machine direction, of each region in which one of said cut lines is to be formed, wherein each of said first fastener elements has an outer end adjacent the first side edge and an opposite, inner end located inwardly in the cross direction from the outer end;

forming a pair of continuous slits in said web on opposite sides, as viewed in said machine direction, of said region, wherein each of said continuous slits is located between said region and one of said first fastener elements, and extends continuously in said cross direction from a first end located adjacent the first side edge to a second end located inwardly of the inner ends of said first fastener elements;

attaching a fastener base sheet to said web so that the fastener base sheet extends in said machine direction across said region and said slits, wherein the fastener base sheet has thereon a pair of second fastener elements each releasably engaged with one of said first fastener elements and is attached to said web through releasable engagement of respective said second fastener elements with respective said first fastener elements;

forming notches in said web so that each of the notches extends from the first side edge to the first end of one of said slits, respectively;

forming, in said web and along the cut line to be form, a middle opening which defines the leg holes of the adjacent pull-on disposable wearing articles to be made;

folding said web in two in said cross direction with said second surface inside so that an area of said web adjacent the second side edge overlays said region;

bonding said area to said fastener base sheet; and after said bonding, severing said web together with said fastener base sheet along said cut line;

wherein a peripheral edge of said middle opening intersects the slits in vicinity of the second ends of the slits to define a cut-away piece of said web, and said cut-away piece corresponds to said region and is surrounded by the slits, the notches at the first ends of the slits, and the peripheral edge of said middle opening;

said method further comprising:

bonding said cut-away piece to the fastener base sheet to retain said cut-away piece;

wherein said bonding comprises indirectly bonding said area to the fastener base sheet via said retained cut-away piece.

2. A method of continuously making pull-on disposable wearing articles, said method comprising:

feeding a web in a machine direction, said web having opposite first and second surfaces and opposite first and second side edges that extend in said machine direction, folding said web in two in a cross direction orthogonal to said machine direction while feeding said web, and severing said folded web along cut lines, which extend in said cross direction, into individual pull-on disposable wearing articles each having a waist-hole and a pair of leg-holes so that these pull-on disposable wearing articles are successively arranged side by side in said machine direction, said method further comprising:

attaching a pair of first fastener elements to the first surface of said web on opposite sides, as viewed in said machine direction, of each region in which one of said cut lines is to be formed, wherein each of said first fastener elements has an outer end adjacent the first side edge and an opposite, inner end located inwardly in the cross direction from the outer end;

forming a pair of continuous slits in said web on opposite sides, as viewed in said machine direction, of said region, wherein each of said continuous slits is located between said region and one of said first fastener elements, and extends continuously in said cross direction from a first end located adjacent the first side edge to a second end located inwardly of the inner ends of said first fastener elements;

attaching a fastener base sheet to said web so that the fastener base sheet extends in said machine direction across said region and said slits, wherein the fastener base sheet has thereon a pair of second fastener elements each releasably engaged with one of said first fastener elements and is attached to said web through releasable engagement of respective said second fastener elements with respective said first fastener elements;

forming, for each pair of said slits, a single notch in said web so that the notch extends from the first side edge to the first ends of both said slits;

forming, in said web and along the cut line to be form, a middle opening which defines the leg holes of the adjacent pull-on disposable wearing articles to be made;

folding said web in two in said cross direction with said second surface inside so that an area of said web adjacent the second side edge overlays said region;

bonding said area to said fastener base sheet; and after said bonding, severing said web together with said fastener base sheet along said cut line;

wherein a peripheral edge of said middle opening intersects the slits in vicinity of the second ends of the slits to define a cut-away piece of said web, said cut-away piece corresponds to said region and is surrounded by the slits, the notches at the first ends of the slits, and the peripheral edge of said middle opening, and the middle opening is bisected by the cut line;

said method further comprising:

bonding said cut-away piece to the fastener base sheet to retain said cut-away piece;

wherein said bonding comprises indirectly bonding said area to the fastener base sheet via said retained cut-away piece.

3. A method of continuously making pull-on disposable wearing articles, said method comprising:

feeding a web in a machine direction, said web having opposite first and second surfaces and opposite first and second side edges that extend in said machine direction, folding said web in two in a cross direction orthogonal to said machine direction while feeding said web, and severing said folded web along cut lines, which extend in said cross direction, into individual pull-on disposable wearing articles each having a waist-hole and a pair of leg-holes so that these pull-on disposable wearing articles are successively arranged side by side in said machine direction, said method further comprising:

forming, in said web and along each of the cut lines to be form, a middle opening which defines the leg holes of the adjacent pull-on disposable wearing articles to be made and which is bisected by the cut line;

attaching a pair of first fastener elements to the first surface of said web on opposite sides, as viewed in said machine direction, of a region in which said cut line is to be formed, wherein each of said first fastener elements has an outer end adjacent the first side edge and an opposite, inner end located inwardly in the cross direction from the outer end;

forming a pair of continuous slits in said web on opposite sides, as viewed in said machine direction, of said region, wherein each of said continuous slits is located between said region and one of said first fastener elements, and extends continuously in said cross direction from a first end located adjacent the first side edge to a second end located inwardly of the inner ends of said first fastener elements but outwardly of a peripheral edge of said middle opening;

attaching a fastener base sheet to said web so that the fastener base sheet extends in said machine direction across said region and said slits, wherein the fastener base sheet has thereon a pair of second fastener elements each releasably engaged with one of said first fastener elements and is attached to said web through releasable engagement of respective said second fastener elements with respective said first fastener elements;

forming first notches in said web so that each of the first notches extends from the first side edge to the first end of one of said slits, respectively;

forming second notches in said web so that each of the second notches extends from the peripheral edge of the middle opening to the second end of one of said slits, respectively;

folding said web in two in said cross direction with said second surface inside so that an area of said web adjacent the second side edge overlays said region;

bonding said area to said fastener base sheet; and after said bonding, severing said web together with said fastener base sheet along said cut line;

wherein a peripheral edge of said middle opening intersects the slits in vicinity of the second ends of the slits to define a cut-away piece of said web, and said cut-away piece corresponds to said region and is surrounded by the slits, the notches at the first ends of the slits, and the peripheral edge of said middle opening;

said method further comprising:

bonding a cut-away piece, which corresponds to said region and is surrounded by the slits, the notches at the first and second ends of the slits, and the peripheral edge of said middle opening, to the fastener base sheet to retain said cut-away piece;

wherein said bonding comprises indirectly bonding said area to the fastener base sheet via said retained cut-away piece.

* * * * *